(12) United States Patent
Irion

(10) Patent No.: US 7,662,095 B2
(45) Date of Patent: Feb. 16, 2010

(54) ENDOSCOPE PROVIDED WITH A LIGHTING SYSTEM AND A COMBINED IMAGE TRANSMISSION

(75) Inventor: Klaus Irion, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 621 days.

(21) Appl. No.: 11/099,244

(22) Filed: Apr. 5, 2005

(65) Prior Publication Data

US 2005/0277810 A1 Dec. 15, 2005

Related U.S. Application Data

(63) Continuation of application No. PCT/EP2003/010653, filed on Sep. 25, 2003.

(30) Foreign Application Priority Data

Oct. 5, 2002 (DE) ................................ 102 46 521

(51) Int. Cl.
*A61B 1/00* (2006.01)
(52) U.S. Cl. ................... 600/181; 600/160; 600/476
(58) Field of Classification Search ................ 600/181, 600/182, 179, 160, 109, 476–478
See application file for complete search history.

(56) References Cited

U.S. PATENT DOCUMENTS

| | | | | |
|---|---|---|---|---|
| 4,919,112 A | * | 4/1990 | Siegmund | 600/136 |
| 5,042,494 A | * | 8/1991 | Alfano | 600/477 |
| 5,048,030 A | * | 9/1991 | Hiiro | 372/68 |
| 5,298,741 A | | 3/1994 | Walt et al. | 250/227.23 |
| 5,438,420 A | * | 8/1995 | Harwick et al. | 356/440 |
| 5,557,408 A | * | 9/1996 | Kanaya | 356/514 |
| 5,689,602 A | * | 11/1997 | Arai | 385/119 |
| 5,754,291 A | * | 5/1998 | Kain | 356/338 |
| 5,813,987 A | * | 9/1998 | Modell et al. | 600/473 |

(Continued)

FOREIGN PATENT DOCUMENTS

DE 1 746 649 6/1957

(Continued)

OTHER PUBLICATIONS

Rochelle Prescott, Optical Principle of Endoscopy, Journal of Medical Primatol 5, pp. 133-147, 1976.

*Primary Examiner*—John P Leubecker
(74) *Attorney, Agent, or Firm*—St. Onge Steward Johnston & Reens LLC

(57) ABSTRACT

The invention relates to an endoscope used for lighting and visualizing the fields of an object in cavities. The inventive endoscope comprises a lighting unit and an image transmitting system provided with an optical lens on the distal side thereof and with an optical eyepiece or a filming unit which are used as an observation system on the proximal side thereof. Said endoscope is characterized in that an optical dividing element for complementary light polarization or for wavelength bands and the complementary polarization is inserted between the lighting unit, the image transmitting system, and the visualizing system in such a way that the light emitted by the lighting unit can be injected into the image transmitting system. The dividing element for the complementary light polarization is combined with a quarter-wave plate which is arranged before the lens on the distal side thereof.

20 Claims, 4 Drawing Sheets

U.S. PATENT DOCUMENTS

| | | | |
|---|---|---|---|
| 6,028,622 A * | 2/2000 | Suzuki | 348/65 |
| 6,063,024 A * | 5/2000 | Yamamoto | 600/160 |
| 6,097,744 A * | 8/2000 | Takigawa et al. | 372/34 |
| 6,110,106 A * | 8/2000 | MacKinnon et al. | 600/181 |
| 6,174,291 B1 * | 1/2001 | McMahon et al. | 600/564 |
| 6,226,119 B1 * | 5/2001 | Kurata | 359/380 |
| 6,366,403 B1 * | 4/2002 | Kurtz et al. | 359/487 |
| 6,485,413 B1 * | 11/2002 | Boppart et al. | 600/160 |
| 6,495,363 B2 * | 12/2002 | Bogdanov | 506/39 |
| 6,565,210 B2 * | 5/2003 | Kobayashi et al. | 351/214 |
| 6,658,315 B2 * | 12/2003 | Chan | 700/121 |
| 6,687,010 B1 * | 2/2004 | Horii et al. | 356/479 |
| 6,949,069 B2 * | 9/2005 | Farkas et al. | 600/178 |
| 2002/0087047 A1 * | 7/2002 | Remijan et al. | 600/109 |

FOREIGN PATENT DOCUMENTS

| | | |
|---|---|---|
| DE | 35 42 207 A1 | 6/1987 |
| DE | 196 39 653 A1 | 4/1998 |
| JP | 11019026 A | 1/1999 |
| JP | 2002023067 | 1/2002 |
| JP | 2002023067 A * | 1/2002 |
| WO | WO 91/15793 | 11/1991 |

* cited by examiner

US 7,662,095 B2

ENDOSCOPE PROVIDED WITH A LIGHTING SYSTEM AND A COMBINED IMAGE TRANSMISSION

This application is a continuation of PCT/EP2003/010653 filed Sep. 25, 2003 which designates the United States and claims priority of German Application No. 102 46 521.5 filed Oct. 5, 2002.

FIELD OF THE INVENTION

The invention relates to an endoscope used for lighting and visualizing the fields of an object in cavities. The inventive endoscope comprises a lighting unit and an image transmitting system provided with an optical lens on the distal side thereof and with an optical eyepiece or a filming unit which are used as an observation system on the proximal side thereof.

Endoscopes of this type in rigid and flexible design are known and described, for instance, in the paper "Optical Principles of Endoscopy" by R. Prescott, J. Med Primatol. 5 (1976): 133-147, in their fundamental characteristics. All endoscopes of this kind known to date include, besides the transmitting system for image capture and image transmission, a separate system for light transmitting to illuminate the field of the object to be observed. The field can be in the cavity of a technological or biological subject.

Among small-caliber endoscopes in particular, the so-called mini-endoscopes, these separate transmitting systems lead to an overproportionate increase in diameter. Another important reason is that both transmitting systems must be isolated from one another both optically and mechanically in order, first, to prevent inductive disturbance of the light from the illuminating system to the image transmitting system and, second, to maintain a stable and autoclave-resistant total system.

The thinnest image transmitting systems are already in the vicinity of 200 micrometers and possess a resolution of approximately 6000 image elements. If one were to create a conventional mini-endoscope on this basis, an additional light control system becomes necessary, one that is adapted in optical isolation, coaxially in part, to the image conductor. Most often the coaxially constructed system is also surrounded by a coating for mechanical stability and to secure the light-conducting fibers and the autoclavability. The diameter of the entire mini-endoscope, with these measures, amounts to more than twice the diameter of the image conductor. With larger endoscopes, this ratio is not quite so extreme, but here too there is a significant increase owing to the separate light canal. With a rigid endoscope with rod lenses, the lens system, for instance, has a diameter of about 2.8 mm and the entire system with light and mechanical coating approximately 4.0 mm.

For many applications there is a desire to improve the ratio between the image conductor and the entire diameter of the endoscopic system. In particular, in dental medicine there are applications in which extremely thin and flexible endoscopes are required, for instance in the inspection of the artificially opened dental root canal as far as the apex, or in the inspection of the spinal canal.

From DE 196 39 653 A1, we have endoscopes for visualizing biological tissue that are used in fluorescent endoscopy. Light is applied with a short-wave stimulation and fluorescent light of a long-wave emission is received as an image and endoscopically transmitted. The fluorescent light contains information that can be used to characterize the tissue. The stimulus light is radiated onto the tissue by a separate light conductor parallel to the transmission of the fluorescent light. The degrees of transmission in the light-admitting and image-producing part are selected so that the image of the tissue area to be illuminated with stimulation light is produced by means of fluorescent light and reflected lighting light, and both portions contributing to the image production are produced, in terms of their wavelength and their intensity, in such a way that no reciprocal disturbance occurs.

In this application, also, a general development aim consists in further reducing the endoscope diameters in order to have a thinner instrumentation for reducing traumatization of the patient. Often, however, in opposition to this aim, the light intensity radiated by the light conductors is no longer great enough for sufficient fluorescent stimulation and the fluorescent radiation captured by the image conductor is insufficient for the sensitivity of the detection system.

Other systems for examining body cavities have an image formation system consisting of an optical lens and an optical eyepiece that allows only relatively short image formation paths to be encompassed.

A Kopol microscope for visualizing processes in body cavities of living organisms is described in DE 1 746 649 U. The device contains a lighting unit, an optical lens, and an optical eyepiece. The illuminating light is inserted by means of an interference-mirror filter into the observation ray path between the optical lens and the eyepiece. For fluorescent observation a blue filter is inserted into the lighting unit and a blocking filter for residues of the blue stimulation ray is arranged before the eyepiece. For clarified observation a polarization filter is inserted into the observation unit and a polarization-blocking filter is placed before the eyepiece for the portions of the polarizing observation rays reflected inside the device. The tube to be inserted into the body cavity with the lens is very short and has a relatively large diameter.

DE 35 42 207 A1 describes a device to carry out medical examinations in body cavities. The device contains a filming unit aimed at the photographic area to be examined. In one embodiment the light for lighting the photographic area is guided to the object, coaxially to the optical axis, by means of a semi-transparent mirror arrange before the camera. A polarization filter for producing special effects can be placed behind the semi-transparent mirror. The lighting system is positioned in a short tube, with relatively large diameter, placed on the camera.

JP 2002-023 067 A describes an optical system for an electronic endoscope. The system contains, on the object side, an object lens, before which a quarter-wave plate and a polarizer are arranged. The polarizer consists of two rectilinear prisms forming a cube, and the surfaces of the prisms lying on one another contain a polarization foil. The illuminating light is directed at the polarizer by a light conductor; the illuminating light is polarized linearly on the polarization foil and circularly by the quarter-wave plate. The ray reflected by the object and received by the object is in turn linearly polarized vertically to the illuminated ray in known manner by the quarter-wave plate and is reflected on the polarization foil in the direction toward an electronic filming unit. The diameter of the system portion to be introduced into the body cavity is relatively large because of the dimensions of the polarizer and the contiguous filming unit.

SUMMARY OF THE INVENTION

It is therefore the aim of the invention to create an endoscope with a further reduced diameter in which lighting directed from outside can be of sufficient intensity without being required to restrict the diameter of the image transmitting system required for image transmission.

This aim is fulfilled according to the invention with an endoscope of the aforementioned type in that on the proximal side an optical dividing element is inserted for complementary light polarizations or for complementary wavelength bands and light polarization between the lighting unit, the image transmitting system, and the visualizing system in such a way that the illumination light produced by the lighting unit can be inserted into the image transmitting system. Here, because of an insufficient separation sharpness of the dividing element, it is generally not possible to avoid having portions of the illuminating light also enter the visualizing system. Analogously to the fluorescent endoscopy described in DE 196 39 653 A1, this is even an advantage. In principle, however, one aspires to the fullest possible separation of the complementary light portions.

By inserting a small quarter-wave plate before the optical lens on the distal side, the effectiveness of the separation according to light polarizations on the dividing element is substantially improved.

If the dividing element is optimized for complementary light polarizations, then additional spectral filters can be provided for the short-wave and longer-wave spectral area. Of course, it is also possible to provide special spectral filters to increase the separation sharpness of a spectrally and polarization-optically separating dividing element and special polarization filters to increase the separation sharpness of a purely polarization-optical dividing element or of a spectrally and polarization-optical dividing element.

Additional advantageous embodiments of the invention can be derived from the characteristics of the additional subsidiary claims.

Because of the arrangement of the dividing element, the entire cross-section of the image transmitting system is now available for transmitting the illuminating light. Because this cross-section is usually greater than the cross-section of an otherwise customary separate light transmitting system, the conditions for transmitting a sufficient light intensity for fluorescent stimulation are substantially improved. By omitting a separate light-conducting system on the dividing element, an effective separation of the lighting unit from the observation system is ensured.

The principles of an endoscopic fiber bundling system with a post-mounted cordierite beam divider are described in U.S. Pat. No. 5,298,741A. Here an arrangement is described in which one or more fluorescent materials are applied to the surface on the distal end of the fiber bundling system and form a reaction with the adjacent bodily fluids or with a tissue component and thus are stimulated to a concentration-dependent fluorescence when they are radiated with light of an appropriate wavelength. The stimulation light is selected by the stimulation filter and inserted by means of a cordierite dividing into the fiber bundling system. The fluorescent light arising at the distal end of the fiber bundling system is transmitted by the same fiber bundling system back to the proximal end and by the cordierite dividing and an additional appropriate detection filter is directed to an evaluation system. The system is not appropriate for endoscopic observation of a cavity.

It has been shown, surprisingly, that in the proximal-side arrangement of an optical dividing element for complementary light polarization both the necessary light for illumination in the one direction and the light coming out of the cavity for observation in the other direction can be transmitted and, after separation, can be evaluated and observed on the dividing element without mutual disturbance. Here, advantageously, it is possible as image transmitting systems to provide multi-fiber image-conducting systems with level end surfaces, image transmitting systems made up of rod lenses with bent end surfaces, or else gradient-index rod lenses with level end surfaces.

The use of complementary wavelength areas for lighting and observations is especially advantageous in processes of fluorescent diagnosis on biological tissue. The lighting normally proceeds at wavelengths of close UV up to 430 or 450 nm, and the observation in the respective adjoining longer-wave spectral area.

On the other hand, it can also be desirable to be able to observe the object field in white light. The additional illumination light required for lighting the object field can usually also be guided onto the distal end of the endoscope by a separate, relatively thin-caliber fiberoptic lighting system. For observation in white light, on the proximal side between the image transmitting system and the dividing element it is possible to insert a neutral divider with appropriate dividing ratio which uncouples one part of the returning light from the beam path for observation.

However, if lighting and observation occur in the same wavelength area, then the lighting light and the observation light can be linearly polarized vertically to one another. To avoid disturbing reflexes, it is advantageous here to install a quarter-wave plate before the distal end of the image transmitting system a quarter-wave plate. This plate, in a manner essentially known in the state of the art, produces circularly polarized light from linearly polarized light. After reflection on the tissue to be observed, the circularly polarized light on the quarter-wave plate is transformed into 90-degree rotated linearly polarized light, which is separated on the dividing element for observation.

The illumination light is usually substantially brighter in comparison to the observation light. Reflections of the illumination light on glass/air surfaces or cemented surfaces within the image transmitting system can thus be in the same order of magnitude as the observation light reflected on the tissue. For an optimal separation of the observation light from the illumination light it is therefore advantageous to design the dividing element both for a separation by wavelength areas and by light polarization.

The optical dividing element, in essentially familiar manner, can advantageously be constructed from two equal-sided rectilinear prisms forming a cube, in which the hypotenuse surface of one of the rectilinear prisms is coated with a polarization-optic or with a spectral and polarization-optic filter layer and where in each case an individual appropriate cathetus surface is related to the lighting unit, the image transmitting system, and the observation system. Complementary polarization or spectral filter elements can be related to the cathetuses.

When an image transmitting system with a proximally plane end surface is used, the cube with the related cathetus surface can be applied to this end surface. A surface-image sensor with integrated semiconductor-based loading or electron duplicator and possibly a cooling element can be linked to the cathetus surface for the observation system. A laser diode matrix as light source can be linked to the cathetus surface for the lighting unit. Such an arrangement of the lighting and observation means on the dividing element allows for an extremely compact construction of the endoscope.

The lighting unit, the dividing element, and the observation system can in particular be combined in a single housing unit which is provided with an adapter for replaceable insertion of the image transmitting system on the related cathetus surface of the dividing element. In this manner it is also possible to use one-way image transmitting systems. As light sources it is advantageous to employ xenon, mercury-vapor, or halide lamps, or else a laser system can be inserted into the housing unit. In particular, with the help of a laser system it is possible to produce light intensities of the strength necessary for photodynamic therapy (PDT), that is, for the selective destruction of tissue during visual observation.

The dividing element can also be positioned replaceably in the housing unit for adaptation to varying observation processes.

The illustrations show schematic depictions of embodiments and are described hereafter with reference to the figures.

DETAILED DESCRIPTION OF THE DRAWINGS

In FIG. 1 is shown the basic principle of an endoscope with an inventive inserted dividing element in different variants.

Figures 1A, 1B, 1C:
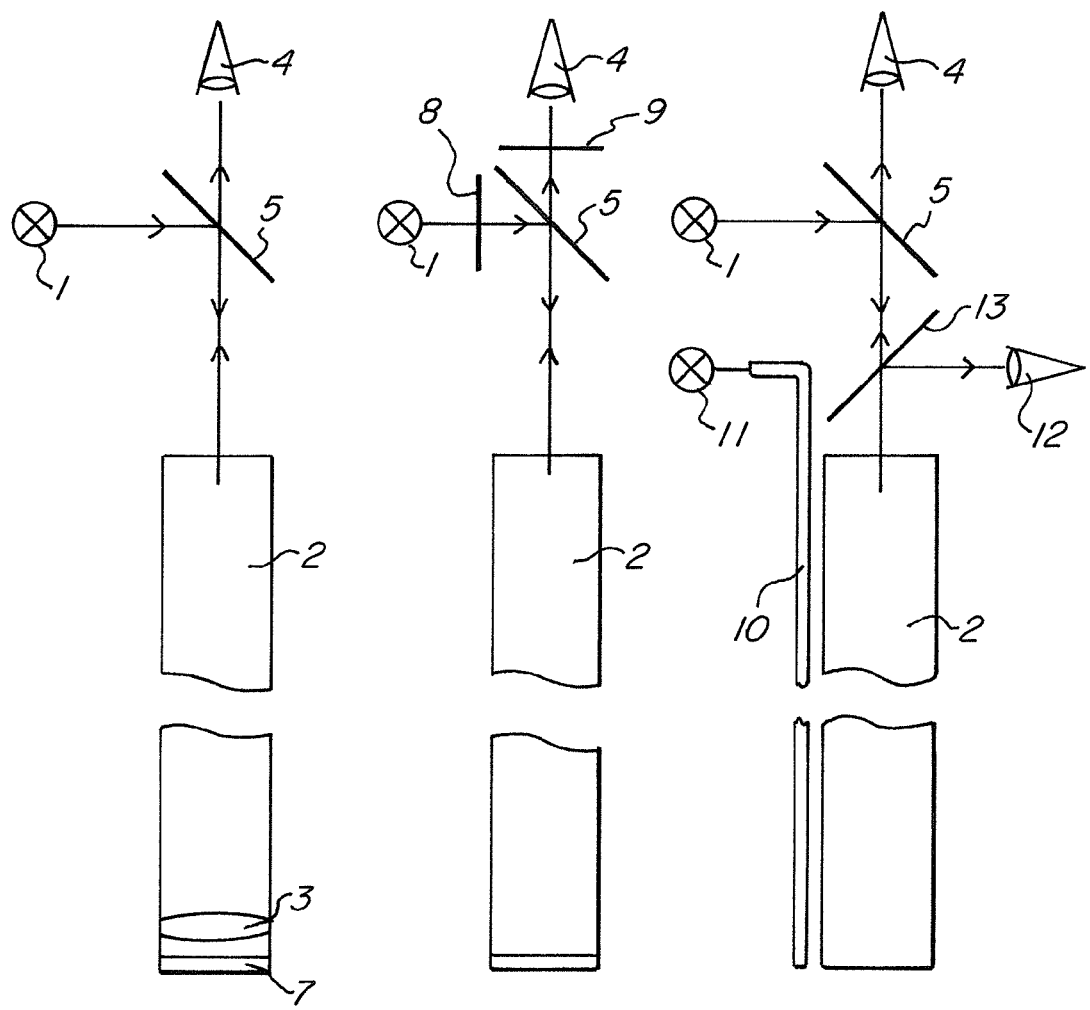
FIG. 1a shows an endoscope with dividing element.
FIG. 1b shows an endoscope dividing element and additional filter elements.
FIG. 1c shows an endoscope with additional white light illumination.

The endoscope seen in FIG. 1a consists, first, of a lighting unit 1 and an image transmitting system 2, to which a lens system 3 is linked on the distal side and an observation system 4 is linked on the proximal side. On the proximal side, moreover, a dividing element 5 is positioned in such a way that, first, the illumination light produced by the lighting unit 1 can be into the image transmitting system 2 and, second, the light reflected on an object field 6 in a cavity and conveyed back by the image transmitting system 2 is directed to the observation system 4. Here the dividing element 5 has the characteristic of influencing in different ways mutually complementary light polarizations or wavelength areas and light polarizations in reflection and transmission. If the dividing element 5 is configured in reflection and transmission in each case for a separation of linear polarizations arranged vertically to one another, it is advantageous to position quarter-wave plate upstream from the optical lens 3 on the distal side.

In the endoscope in FIG. 1b, complementary filter elements 8, 9 are related to the dividing element 5 on the lighting side and on the observation side. Thus the dividing element 5 can be optimized for instance for the separation of complementary light polarizations and wavelength bands. In this case the filter element 8 on the lighting side can be configured as a polarizer and the filter element 9 on the observation side as an analyzer. If, on the other hand, the dividing element 5 is optimized for the separation of complementary light polarizations, then the filter element 8 can advantageously be configured as a spectral filter for a short-wave spectral area and the filter element 9 for a longer-wave spectral area, if the arrangement is to be used for a fluorescent analysis.

In the arrangement in FIG. 1c, an additional fiberoptic lighting system 10 is provided, with a white light source 11 for lighting the object field 6 to be observed in the cavity. A white light portion is therefore applied over the light reflected by the object field 6 and conveyed back by the image transmitting system 2; this white light portion, for instance, also makes visible the environment of an object detail that is to be stimulated to fluorescence. To make this image accessible to an observation 12, a neutral divider 13 is provided on the proximal-side outlet of the image transmitting system 2. On the following dividing element 5 the white light portion is suppressed, as far as the possibly present longer-wave spectral portions, which fall within the spectral area of the fluorescent stimulation.

Figure 2:
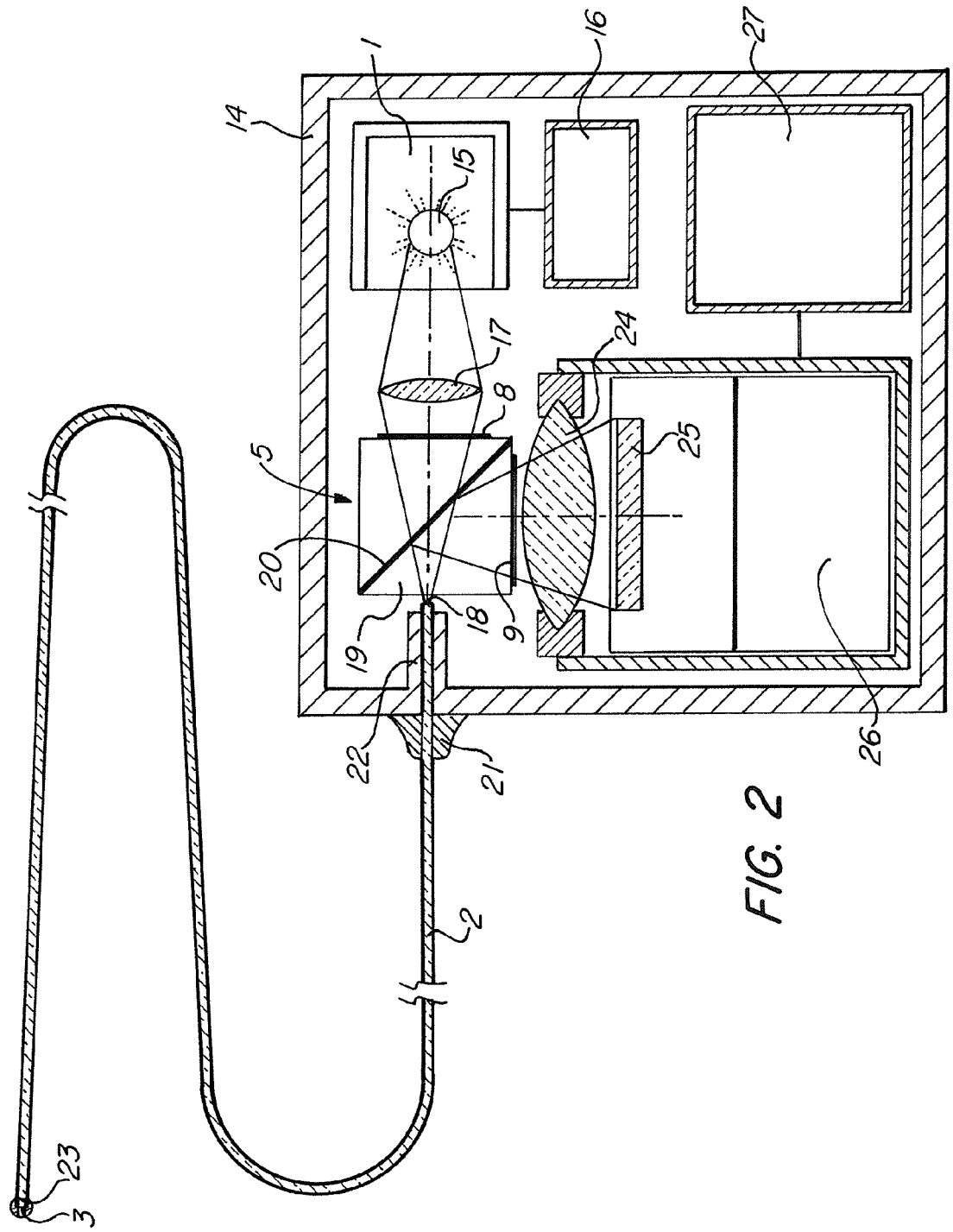
FIG. 2 shows an embodiment with housing unit.

In the embodiment shown in FIG. 2, a lighting unit 1 with lamp 15 and lamp control unit 16, as well as a collector lens 17, is positioned in a device unit 14. As lamp 15, a xenon, mercury-vapor, or halide lamp or else a laser or laser diode system can be used in particular. The collector lens 17 forms an image of the radiation of the lamp 15 by means of a dividing element 5 all the way to a proximal end surface 18 of an image transmitting system 2.

The dividing element 5 consists of two equal-sided rectilinear prisms 19, which are combined with their hypotenuse surfaces and thus form a cube. The hypotenuse surfaces of the rectilinear prisms 19 are covered with a polarization-optic or spectral and polarization-optic dividing layer 20. The spectral dividing layer 20 is intended to be transparent, for instance, for a pre-selected wavelength area out of the emission spectrum of the lamp 15 and to be reflecting for a complementary, i.e. long-wave, wavelength band. The reflected radiation portion is directed against the wall of the housing unit 14 and absorbed there, for instance in a flat back coating as a beam trap.

As a polarization-optical dividing layer it is possible, for instance, to provide a polarization foil, which linearly polarizes the radiation of the lamp 15 passing through the foil. A good polarization can be produced over a broad wavelength area, so that quasi-white light is into the image transmitting system 2. Of course, a combination in the spectral boundary of the wavelength area and of the linear polarization is also possible, which even basically approximates the spectral dependency of the polarization foil. The dividing layer 20 also be combined with selected complementary filter elements 8, 9 depending on the application purpose.

The image transmitting system 2 can preferably be configured as a multi-fiber image conductor. Such a system is relatively flexible and generally possesses a high spectral transmission if the fibers are produced from quartz glass. Therefore greater lengths can also be produced, without significant reduction in light transmission. The systems, in view of the total diameter, have a relatively good image quality. The quartz glass, in addition, has no fluorescence of its own. The end surfaces are generally level.

The length of the multi-fiber image conductor that can be produced can be selected in such a way that the proximal end surface lies outside the sterile patient area. On the basis of the relatively low costs of the multi-fiber image conductor because of its simply and automated production, it is therefore advantageous to position the image conductor so that it can be separated from the device unit 14 and can be used as a one-way product. In this way it is possible to avoid the cleaning, sterilization, and contamination problems that arise from every usage.

In the embodiment in FIG. 2 the image transmitting system 2 is provided on the proximal end with a plug-in device 21 by which it can be secured in an adapter 22 in the housing unit 14 in its position with respect to a cathetus surface of the dividing element 5.

The image transmitting system 2 is provided on its distal end surface 23 with a lens system 3. The lens system 3 can, for instance, be configured as a gradient lens which is soldered onto the end surface 23 in order to prevent fluorescence of its own by an adhesive. When linearly polarized light is used, a quarter-wave plate (not illustrated) can be applied on the level end surface 23.

The visualization light separated by the lens system 3 sheds light on a particular angle area before the lens system 3. The system is so configured that an image with an image angle corresponding, at least for the most part, to the angle of lighting is captured by the distal-side lens system 3.

The image received by the lens system 3 consists, in the case of the fluorescent diagnosis, of a radiation with a wavelength that is complementary to the illumination light. The radiation belonging to the image is reflected on the dividing layer 20 and conveyed to the observation system. Likewise, with linear polarization of the observation light, the radiation belonging to the image will be polarized vertically to it and thus also reflected on the dividing layer 20.

The illustrated observation system consists of a field lens 24 and, for instance, a surface image sensor 25 according to the principle of single photon detection (SPD principle). This image sensor has the advantage that the means for image reinforcement are integrated into the semiconductor chip, so that a light and compact structure is possible for the image formation. In cooperation with the image transmitting by a multi-fiber image conductor, a two-dimensional PSD image receptor also has the advantage that the image points arising from every individual image fiber partly overlap with image points situated near them, so that a more uniform image results.

A cooling device 26, which is also attached to the SPD image sensor 25, can be for instance a Peltier element or else a container with cooled $CO_2$. To control the image sensor 25 and the cooling device 26, in the housing unit 14 there is also a control device 27. This can also control a monitor (not illustrated) for visual image observation.

Figure 3:
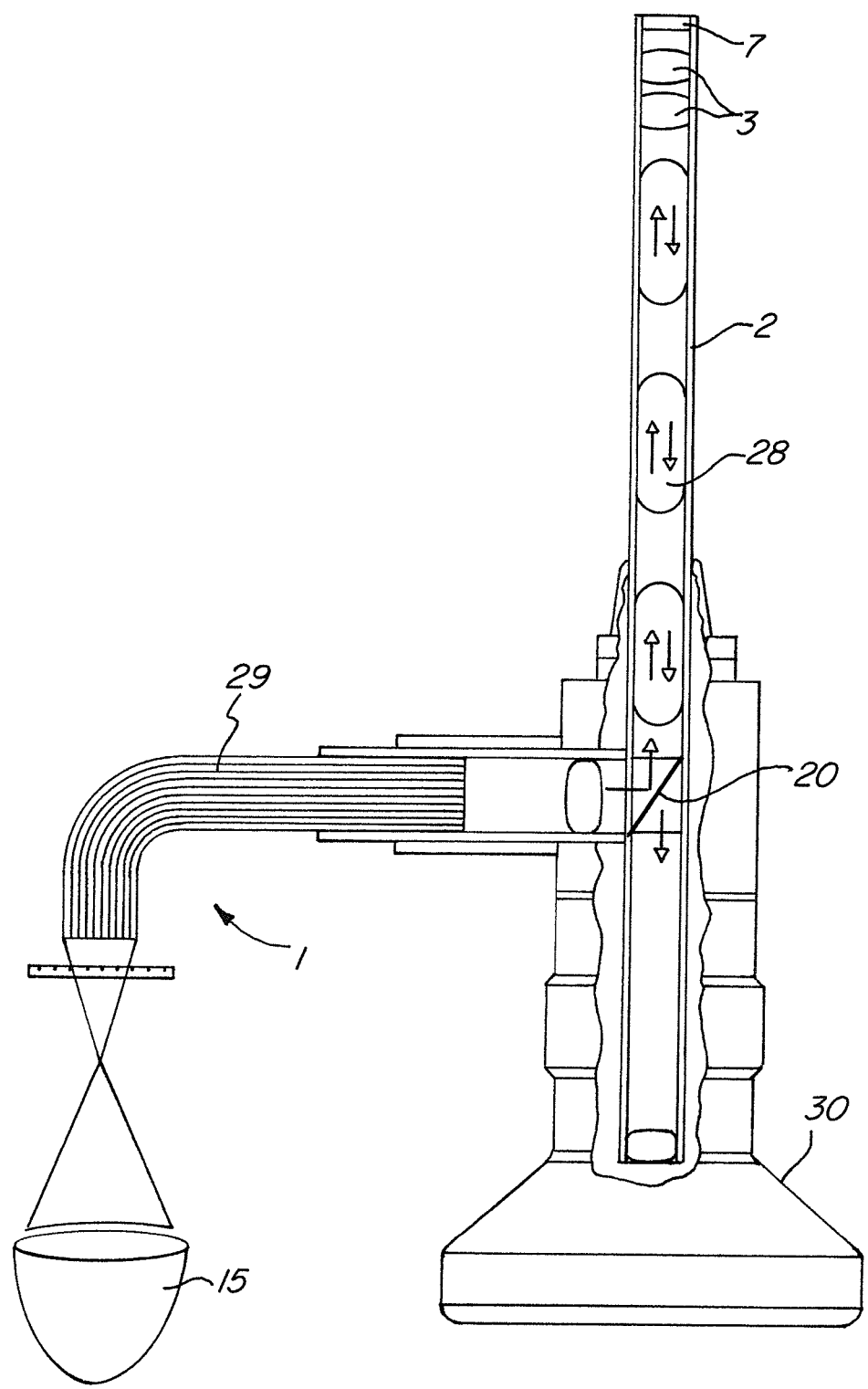
FIG. 3 shows another embodiment of the endoscope.

In the embodiment shown in FIG. 3 the image transmitting system 2 consists of rod lenses 28 with generally curved end surfaces. Their advantage is the very good image quality with a good depth of sharpness and high light transmission. The rod lenses, however, are expensive to produce, cannot be executed to any desired thinness, and often have cement surfaces that tend toward self-fluorescence.

These disadvantages can be avoided if the image transmitting system is constructed with rod lenses of a gradient index material with level end surfaces.

The lighting unit 1 contains a light-conductor bundle 28, which is applied laterally on a viewer housing 30 so that the illumination light is reflected on the dividing surface 20 and the observation 4 occurs in transmitting.

These disadvantages can be avoided if the image transmitting system is constructed with rod lenses of a gradient index material with level end surfaces.

The lighting unit 1 contains a light-conductor bundle 28, which is applied laterally on a viewing housing 30 so that the illumination light is reflected on the dividing surface 20 and the observation 4 occurs in transmitting.

Figure 4:
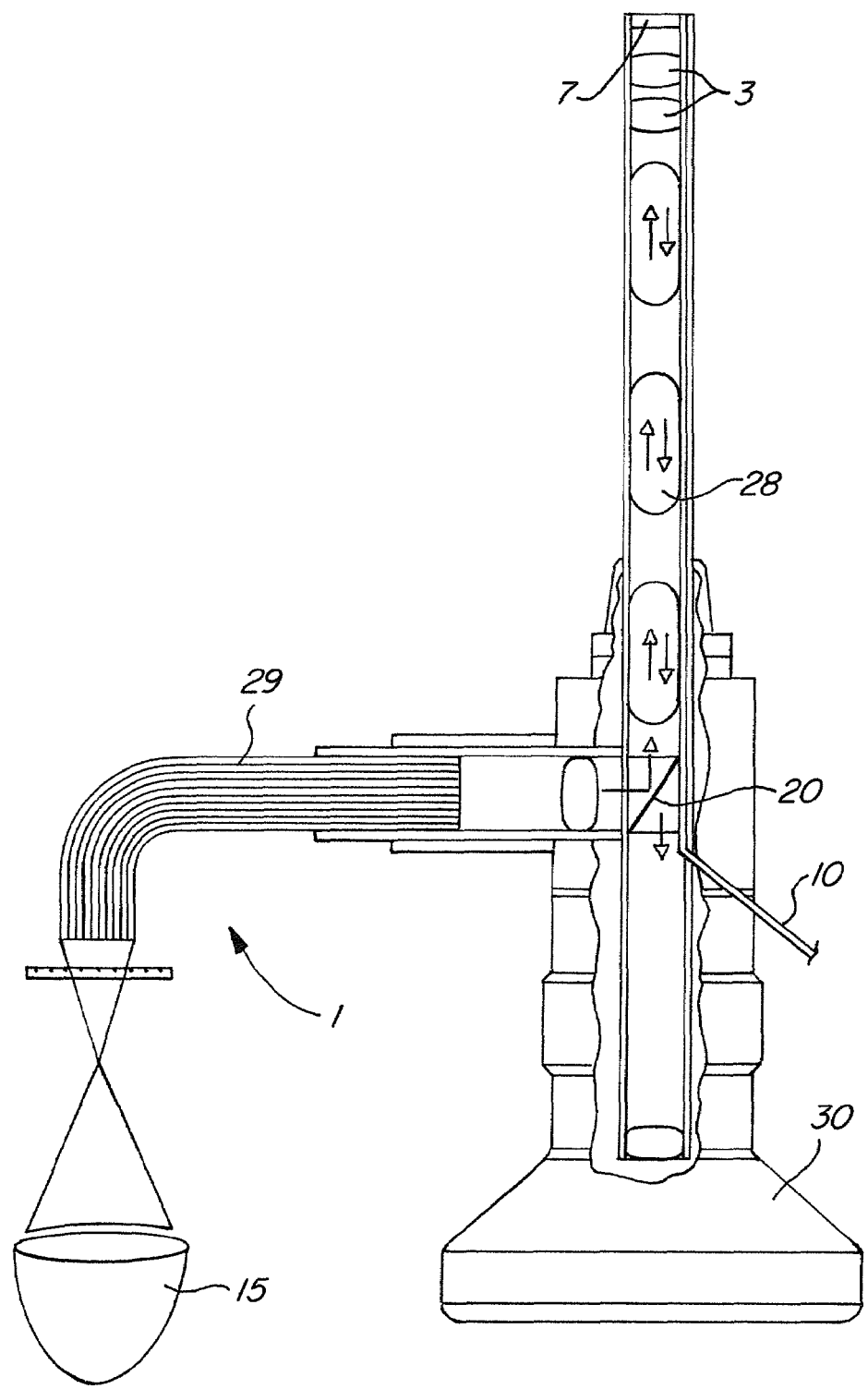
FIG. 4 shows an embodiment with additional white light illumination.

The embodiment shown in FIG. 4 corresponds to the previous one. However, in addition here a fiberoptic lighting system 10 is added for white light illumination. The dimensions of the fiber bundle 10 in comparison to the image transmitting system of the rod lenses 28 makes clear that the total cross-section of the endoscope part to be inserted into a body cavity is not essentially influenced here.

The invention claimed is:

1. An endoscope for lighting and observing object fields in cavities, with a lighting unit and an elongated endoscopic image transmitting system to which are assigned on the distal side an optical lens and on the proximal side an optical eyepiece or a filming unit as an observation system, which on the proximal side contains an optical dividing element which is inserted between the lighting unit, the elongated image transmitting system and the observation system such that the observation light produced by the lighting unit can be coupled into the elongated image transmitting system, the optical dividing element being designed, with respect to reflection and transmission, for mutually complementary light polarizations, characterized in that on the distal side a quarter-wave plate is connected distal of the optical lens and further characterized in that an additional fiberoptic lighting system is provided to illuminate the cavity in white light and on the proximal side between the image transmitting system and the dividing element a neutral divider is inserted to separate a part of the returning light for an additional observation.

2. An endoscope according to claim 1 characterized in that on a side adjacent the lighting unit in addition a first filter element is associated with the dividing-element as a spectral filter for the short-wave spectral range and on a side adjacent the observation system in addition a second filter element is associated as spectral filter for the longer-wave spectral range.

3. An endoscope according to claim 1 characterized in that the image transmitting system is configured as a multi-fiber-image conductor system with level end surfaces.

4. An endoscope according to claim 3, characterized in that the multi-fiber-image conductor system consists of mono-mode fibers.

5. An endoscope according to claim 1 characterized in that the image transmitting system consists of rod lenses with curved end surfaces.

6. An endoscope according to claim 1 characterized in that the image transmitting system comprises gradient index rod lenses with level end surfaces.

7. An endoscope according to claim 1 characterized in that the optical dividing element is made up of two equal-sided rectilinear prisms to form a cube, in which the hypotenuse surface of one of the rectilinear prisms is covered with a spectral and polarization-optical or a polarization-optical dividing layer and where one appropriate cathetus of the dividing element is associated with the image transmitting system and one with the observation system.

8. An endoscope according to claim 7, characterized in that complementary polarization-optical or spectral filter elements are associated with the cathetus surfaces between the lighting unit and the observation system.

9. An endoscope according to claim 7, characterized in that, as the filming unit, a surface-image sensor with integrated semiconductor-based loading or electron duplicator is provided and is associated with a cathetus surface of the dividing element.

10. An endoscope according to claim 9, characterized in that a cooling element is associated with the surface-image sensor.

11. An endoscope according to claim 7, characterized in that, as the lighting unit, a laser diode matrix is provided and is associated with a cathetus surface of the dividing element.

12. An endoscope according to claim 1 characterized in that the lighting unit, the dividing element, and the observation system are combined in a housing unit that is equipped with an adapter for replaceable mounting of the image transmitting system on the related cathetus surface of the dividing element.

13. An endoscope according to claim 12, characterized in that the dividing element is replaceably positioned in the housing unit.

14. An endoscope according to claim 1 characterized in that the lighting unit contains a xenon, mercury-vapor, or halide lamp to produce an incoherent lighting.

15. An endoscope according to claim 1 characterized in that the lighting unit contains a laser system as radiation source.

16. An endoscope for lighting and observing object fields in cavities, with a lighting unit and an elongated endoscopic image transmitting system to which are assigned on the distal side an optical lens and on the proximal side an optical eyepiece or a filming unit as an observation system, which on the proximal side contains an optical dividing element which is inserted between the lighting unit, the elongated image transmitting system and the observation system such that the observation light produced by the lighting unit can be coupled into the elongated image transmitting system, the optical dividing element being designed, with respect to reflection and transmission, for mutually complementary light polarizations, characterized in that the optical dividing element is additionally designed, with respect to reflection and transmission, for mutually complementary wavelength ranges, with the wavelength range which is coupled into the elongated image transmitting system being in the shortwave spectral range, and the wavelength range coupled out into the observation system being in the longer-wave spectral range which follows the shortwave spectral range, characterized in that on the distal side a quarter-wave plate is arranged distal of the optical lens and further characterized in that an additional fiberoptic lighting system is provided to illuminate the cavity in white light and on the proximal side between the image transmitting system and the dividing element a neutral divider is inserted to separate a part of the returning light for an additional observation.

17. An endoscope according to claim 16 characterized in that in addition a first filter element is associated with the dividing element on a side adjacent the lighting unit as a polarizer and on a side adjacent the observation system in addition a second filter element is associated with the dividing-element as an analyzer.

18. An endoscope according to claim 16, characterized in that the dividing element is provided on a side adjacent the lighting unit for the near-UV wavelength range and on a side adjacent the observation system for the visible wavelength range.

19. An endoscope according to claim 18, characterized in that the wavelength range on the side adjacent the lighting unit extends up to approximately 430 nm and the wavelength range on the side adjacent the observation system begins at about 430 nm.

20. An endoscope according to claim 18, characterized in that the wavelength range on the side adjacent the lighting unit extends up to about 450 nm and the wavelength range on the side adjacent the observation system begins at about 450 nm.

* * * * *